US00PP29637P2

(12) United States Plant Patent
Baijens

(10) Patent No.: US PP29,637 P2
(45) Date of Patent: Sep. 4, 2018

(54) ***IBERIS* PLANT NAMED 'SNOWSATION'**

(50) Latin Name: *Iberis sempervirens*
Varietal Denomination: Snowsation

(71) Applicant: Ball Horticultural Company, West Chicago, IL (US)

(72) Inventor: Martijn Baijens, Grootebroek (NL)

(73) Assignee: Ball Horticulture Company, West Chicago, IL (US)

( * ) Notice: Subject to any disclaimer, the term of this patent is extended or adjusted under 35 U.S.C. 154(b) by 0 days.

(21) Appl. No.: 15/731,339

(22) Filed: May 30, 2017

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Anne Marie Grunberg
(74) *Attorney, Agent, or Firm* — Audrey Charles

(57) ABSTRACT

A new and distinct cultivar of *Iberis* plant named 'Snowsation', characterized by its white-colored flowers, medium green-colored foliage, low vigor, and compact-mounded growth habit, is disclosed.

1 Drawing Sheet

Latin name of genus and species of plant claimed: *Iberis sempervirens.*

Variety denomination: 'Snowsation'.

BACKGROUND OF THE INVENTION

The present invention relates to a new and distinct cultivar of *Iberis* plant botanically known as *Iberis sempervirens* and hereinafter referred to by the cultivar name 'Snowsation'.

The new cultivar originated in a controlled breeding program in Venhuizen, The Netherlands during June 2013. The objective of the breeding program was the development *Iberis* cultivars that have a large inflorescence and a compact-mounded growth habit.

The new *Iberis* cultivar is the result of cross-pollination. The female (seed) parent of the new cultivar is the proprietary *Iberis sempervirens* breeding selection coded 9615-3, not patented, characterized by its white-colored flowers, medium green-colored foliage, and moderately vigorous, compact-mounded growth habit. The male (pollen) parent of the new cultivar is 'Tahoe', not patented, characterized by its white-colored flowers, medium green-colored foliage, and moderately vigorous, compact-mounded growth habit. The new cultivar was discovered and selected as a single flowering plant within the progeny of the above stated cross-pollination during May 2014 in a controlled environment in Venhuizen, The Netherlands.

Asexual reproduction of the new cultivar by terminal stem cuttings since May 2014 in Venhuizen, The Netherlands and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Snowsation' as a new and distinct cultivar of *Iberis* plant:

1. White-colored flowers;
2. Medium green-colored foliage;

3. Low vigor; and
4. Compact-mounded growth habit.

Plants of the new cultivar differ from plants of the female and male parents primarily in having a larger diameter inflorescence with tightly spaced florets, and more branches per plant.

Of the many commercially available *Iberis* cultivars, the most similar in comparison to the new cultivar is 'Snow Cone', not patented. However, in side by side comparisons, plants of the new cultivar differ from plants of 'Snow Cone' in at least the following characteristics:

1. Plants of the new cultivar have larger diameter florets than plants of 'Snow Cone'; and
2. Plants of the new cultivar have larger diameter inflorescences than plants of 'Snow Cone'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Snowsation'. The plants were grown in 4.5-inch containers for approximately 23 weeks in a glass-covered greenhouse in Elburn, Ill. Plants were given two pinches before transplant.

DETAILED BOTANICAL DESCRIPTION

Figure 1:
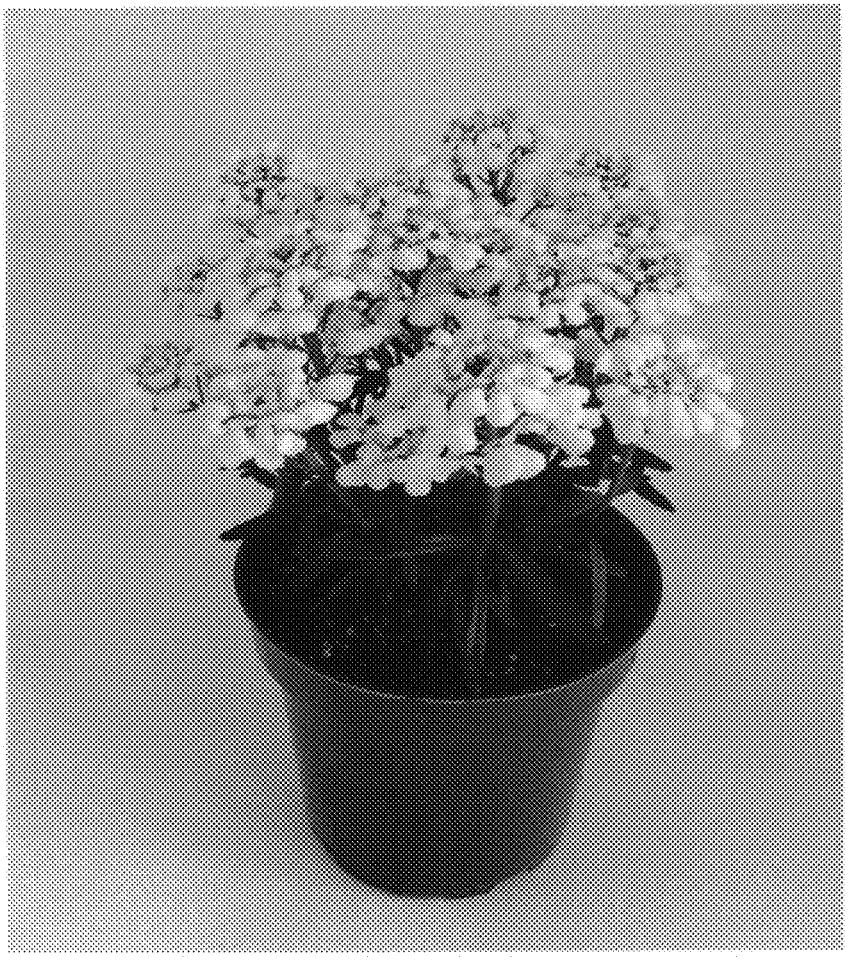
FIG. 1 illustrates a side view of the overall growth and flowering habit of 'Snowsation'.
Figure 2:
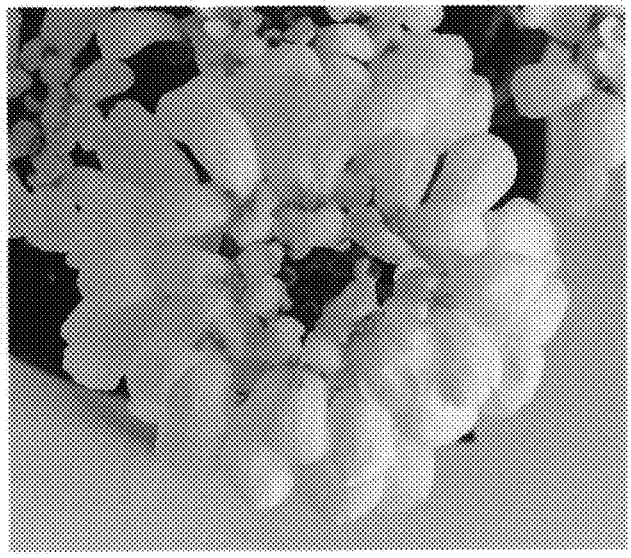
FIG. 2 illustrates a close-up view of the inflorescences of 'Snowsation'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in May 2017 under natural light conditions in West Chicago, Ill.

The following descriptions and measurements describe plants produced from cuttings from stock plants and grown in a glass-covered greenhouse under conditions comparable to those used in commercial practice. The plants were grown utilizing a soilless growth medium in 4.5-inch containers for approximately 23 weeks in Elburn, Ill. Plants were transplanted in late fall from rooted cuttings and were given two pinches before transplant. Greenhouse temperatures were maintained during the winter months at approximately 45° F. to 65° F. (7.2° C. to 18.3° C.) during the day and approximately 35° F. to 45° F. (1.7° C. to 7.2° C.) during the night. For the final 12 weeks, greenhouse temperatures were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Iberis sempervirens* cultivar Snowsation.

Parentage:

*Female parent*.—Proprietary *Iberis sempervirens* breeding selection coded 9615-3, not patented.

*Male parent*.—'Tahoe', not patented.

Propagation:

*Type cutting*.—Terminal stem.

*Time to initiate roots*.—Approximately 12 to 14 days.

*Time to produce a rooted cutting*.—Approximately 35 to 42 days.

*Root description*.—Fine, fibrous.

*Rooting habit*.—Freely branching.

Plant description:

*Commercial crop time*.—Approximately 24 weeks from a rooted cutting to finish in a 15 cm pot, includes 6 to 7 weeks vernalization period.

*Growth habit and general appearance*.—Herbaceous perennial, low growth vigor, compact-mounded.

*Hardiness*.—USDA Zone 4a (−30° F. to −25° F./−34.4° C. to −31.7° C.).

*Size*.—Height from soil level to top of plant plane: Approximately 15.0 cm. Width: Approximately 17.0 cm.

*Branching habit*.—Freely branching, pinching improves basal branching. Quantity of main branches per plant: Approximately 19.

*Branch*.—Shape: Rounded and slightly ribbed. Strength: Strong. Length to base of inflorescence: Approximately 8.5 cm. Diameter: Approximately 2.0 mm. Length of central internode: Approximately 5.0 mm. Texture: Glabrous. Color of young stems: 144A. Color of mature stems: 146B, stems become woody 199B to 199C with age.

Foliage description:

*General description*.—Quantity of leaves per main branch: Approximately 14. Fragrance: None. Form: Simple. Arrangement: Alternate.

*Leaves*.—Aspect: Perpendicular or obtuse angle to stem. Shape: Oblanceolate. Margin: Entire. Apex: Acute. Base: Attenuate, sessile. Venation pattern: Pinnate. Length of mature leaf: Approximately 3.5 cm. Width of mature leaf: Approximately 6.0 mm. Texture of upper and lower surfaces: Glabrous, leathery. Color of upper surface of young and mature foliage: NN137A, midvein 146C, other venation indistinguishable. Color of lower surface of young and mature foliage: 137B, midvein 146B, other venation indistinguishable.

Flowering description:

*Flowering habit*.—'Snowsation' is freely flowering under outdoor growing conditions with substantially continuous blooming from early spring through spring.

*Lastingness of individual flower on the plant*.—Approximately 5 to 7 days.

Inflorescence description:

*General description*.—Type: Corymb. Quantity per plant: Approximately 21. Fragrance: Moderate, pungent. Length or height of terminal corymb: Approximately 3.5 cm. Width of terminal corymb: Approximately 4.0 cm. Length or height of axillary corymb: Approximately 1.5 cm. Width of axillary corymb: Approximately 2.5 cm. Quantity of fully open flowers per terminal corymb: Approximately 18. Quantity of fully open flowers per axillary corymb: Approximately 5.

*Peduncle*.—Strength: Strong. Aspect: Primary erect, axillary acute angle to stem. Length of primary: Approximately 1.5 cm. Diameter of primary: Approximately 2.0 mm. Length of axillary: Approximately 1.1 cm. Diameter of axillary: Approximately 1.0 mm. Texture: Glabrous. Color: 144A.

Flower description:

*Type*.—Small, asymmetrical cruciferous flowers with two larger abaxial petals and two smaller adaxial petals, freely flowering, not persistent, facing outwardly to upright.

*Bud*.—Rate of opening: Generally takes 3 to 4 days for bud to progress from first color to fully open flower.

*Bud just before opening*.—Shape: Globose. Diameter: Approximately 2.0 mm. Color: Sepal centers of 144A with 137A; margins of NN155D; petals of NN155D.

*Corolla*.—Shape: Cruciform lobes with claws surrounded by calyx. Aspect: Facing upward and outward. Length: Approximately 1.3 cm. Width: Approximately 1.4 cm.

*Petals*.—Quantity: 4. Shape: Obovate. Margin: Entire. Apex: Obtuse. Base: Attenuate. Length of abaxial lobe: Approximately 1.0 cm. Width of abaxial lobe: Approximately 7.0 mm. Length of adaxial lobe: Approximately 3.0 mm. Width of adaxial lobe: Approximately 4.0 mm. Length of claw: Approximately 2.0 mm. Width of claw: Less than 1.0 mm. Color of upper surface of lobe when first and fully open: NN155D. Color of lower surface of lobe when first and fully open: NN155D. Color of upper and lower surfaces of claw: NN155D with a midvein of 145A.

*Calyx*.—Shape: Cupped. Diameter: Approximately 5.0 mm.

*Sepals*.—Quantity per flower: 4, distinct. Shape: Elliptic. Margin: Entire. Apex: Obtuse. Base: Truncate. Length: Approximately 4.0 mm. Width: Approximately 2.0 mm. Texture of inner and outer surfaces:

Glabrous. Color of inner and outer surfaces: Centers of 144A with 137A; margins of NN155D.

*Pedicel*.—Strength: Strong, flexible. Aspect: Acute angle to stem. Length: Approximately 1.5 cm. Diameter: Less than 1.0 mm. Texture: Glabrous. Color: 144B.

*Reproductive organs*.—Androecium: Stamen quantity: 6 per flower. Stamen length: Approximately 4.0 mm, 1 pair slightly shorter and inserted lower. Filament color: 155C. Anther shape: Sagittate, dorsifixed. Anther color: 4A. Pollen amount: Moderate. Pollen color: 4D. Gynoecium: Pistil quantity: 1 per flower, ovary superior, flattened orbicular. Pistil length: Approximately 4.0 mm. Stigma shape: Bifid. Stigma color: 145C. Style length: Approximately 2.5 mm. Style color: 145C. Ovary diameter: Approximately 1.5 mm. Ovary color: N144D.

Seed and fruit production: Neither seed nor fruit production has been observed.

Disease and pest resistance: Resistance to pathogens and pests common to *Iberis* has not been observed.

What is claimed is:

1. A new and distinct cultivar of *Iberis* plant named 'Snowsation', substantially as herein illustrated and described.

* * * * *